(12) United States Patent
Sakuta et al.

(10) Patent No.: US 7,955,608 B2
(45) Date of Patent: Jun. 7, 2011

(54) SILICONE COPOLYMER AND COSMETICS COMPRISING THE SAME

(75) Inventors: Koji Sakuta, Annaka (JP); Masahide Hatanaka, Toda (JP); Harukazu Okuda, Sabae (JP)

(73) Assignees: Shin-Etsu Chemical Co., Ltd., Tokyo (JP); Nissin Chemical Industry Co., Ltd., Echizen-Shi (JP)

( * ) Notice: Subject to any disclaimer, the term of this patent is extended or adjusted under 35 U.S.C. 154(b) by 437 days.

(21) Appl. No.: 12/007,932

(22) Filed: Jan. 17, 2008

(65) Prior Publication Data

US 2008/0175809 A1   Jul. 24, 2008

(30) Foreign Application Priority Data

Jan. 19, 2007   (JP) ................. 2007-010661

(51) Int. Cl.
*A61Q 1/00* (2006.01)
*A61Q 5/02* (2006.01)

(52) U.S. Cl. .................... 424/401; 424/70.12

(58) Field of Classification Search .............. None
See application file for complete search history.

(56) References Cited

U.S. PATENT DOCUMENTS

| | | | |
|---|---|---|---|
| 4,985,155 A | 1/1991 | Yamada et al. | |
| 5,603,926 A | 2/1997 | Matsumoto et al. | |
| 6,120,780 A | 9/2000 | Dupuis et al. | |
| 6,649,679 B1 * | 11/2003 | Stockl et al. | 524/253 |
| 2004/0241126 A1 * | 12/2004 | Sakuta | 424/70.12 |

FOREIGN PATENT DOCUMENTS

| | | | |
|---|---|---|---|
| JP | 1-239175 A | | 9/1989 |
| JP | 1-250305 A | | 10/1989 |
| JP | 4-39312 A | | 2/1992 |
| JP | 6-219921 A | | 8/1994 |
| JP | 9-157130 A | | 6/1997 |
| JP | 10-231231 A | | 9/1998 |
| JP | 10-511703 A | | 11/1998 |
| JP | 2006-282599 | * | 10/2006 |
| JP | 2006-282599 A | | 10/2006 |

OTHER PUBLICATIONS

Japanese Office Action for Application No. 2007-010661, dated Apr. 5, 2011.

* cited by examiner

*Primary Examiner* — Jyothsna A Venkat

(74) *Attorney, Agent, or Firm* — Birch, Stewart, Kolasch & Birch, LLP

(57) ABSTRACT

An aqueous composition used for cosmetics, characterized in that the composition comprises 0.5 to 50 wt %, based on weight of the composition, of a copolymer having main chains comprising the repeating units represented by the following formula (1), the repeating units represented by the following formula (2), and the repeating units represented by the following formula (3), said main chains being crosslinked by a compound or oligomer having 2 to 6 (meth)acryl groups

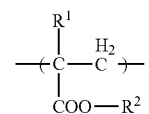

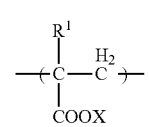

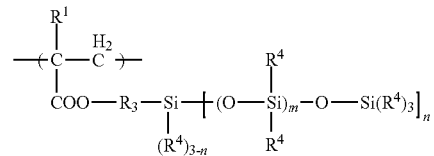

wherein $R^1$ is a hydrogen atom or a hydrocarbon group having 1 to 3 carbon atoms, $R^2$ is a hydrocarbon group having 1 to 24 carbon atoms, $R^3$ is a divalent hydrocarbon group having 1 to 4 carbon atoms, $R^4$ is an aliphatic hydrocarbon group having 1 to 6 carbon atoms or a phenyl group, X is a hydrogen atom, an alkaline metal ion, ammonium ion, or an organic ammonium ion, m is an integer of from 0 to 500 on average, and n is an integer of from 1 to 3.

14 Claims, No Drawings

SILICONE COPOLYMER AND COSMETICS COMPRISING THE SAME

CROSS REFERENCE

This application claims benefit of Japanese Patent application No. 2007-010661 filed on Jan. 19, 2007, the contents of which are hereby incorporated by reference.

FIELD OF THE INVENTION

The present invention relates to a silicone copolymer and cosmetics comprising the same. The silicone copolymer has a crosslinkage to be a good thickener. The copolymer has an organopolysiloxane moiety to be an excellent emulsifier for oil such as silicone oil.

BACKGROUND OF THE INVENTION

Water-soluble or water-swelling polymers such as acrylic polymers, guar gum and cellulose are used to thicken an aqueous composition such as an aqueous solution and an oil-in-water (O/W) type emulsion. An acrylic polymer with its carboxylic groups being neutralized thickens an aqueous solution and oil-in-water (O/W) type emulsion, but makes them sticky. An acrylic polymer having a long-chain alkyl group has not only thickening capability but also capability of emulsifying silicone oils to form O/W type emulsions, but it gives sticky products, too. An acrylic polymer having tris (trimethylsiloxy) moiety as described in Japanese Patent Application Laid-Open No.: 2006-282599 does not have satisfactory thickening capability. Guar gum and cellulose make an aqueous composition not so sticky as the acrylic polymers, but their capability of emulsifying silicone oil into an O/W emulsion is lower than that of the acrylic polymers.

An object of the present invention is therefore to provide a composition for cosmetics which can thicken aqueous compositions without making them sticky, and has an excellent capability of emulsifying silicone oils. Another object of the present invention is to provide cosmetics comprising said composition.

SUMMARY OF THE INVENTION

The present invention is an aqueous composition used for cosmetics, characterized in that the composition comprises 0.5 to 50 wt %, based on weight of the composition, of a copolymer having main chains comprising the repeating units represented by the following formula (1), the repeating units represented by the following formula (2), and the repeating units represented by the following formula (3), said main chains being crosslinked by a compound or oligomer having 2 to 6 (meth)acryl groups

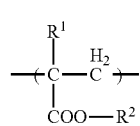

(1)

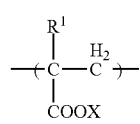

(2)

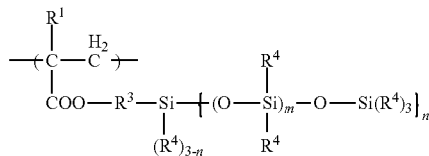

(3)

wherein $R^1$ is a hydrogen atom or a hydrocarbon group having 1 to 3 carbon atoms, $R^2$ is a hydrocarbon group having 1 to 24 carbon atoms, $R^3$ is a divalent hydrocarbon group having 1 to 4 carbon atoms, $R^4$ is an aliphatic hydrocarbon group having 1 to 6 carbon atoms or a phenyl group, X is a hydrogen atom, an alkaline metal ion, ammonium ion, or an organic ammonium ion, m is an integer of from 0 to 500 on average, and n is an integer of from 1 to 3.

The above composition of the present invention comprises a crosslinked polymer to thicken an aqueous solution or an emulsion without making it sticky. Having an organosiloxane moiety, the polymer can emulsify oils very well, particularly silicone oils, to give finely textured cosmetics.

PREFERRED EMBODIMENTS OF THE INVENTION

In the repeating unit represented by the above formula (1), hereinafter referred to as repeating unit (1), $R^1$ is a hydrogen atom or a hydrocarbon group having 1 to 3 carbon atoms, preferably a hydrogen atom or a methyl group. $R^2$ is a hydrocarbon group, preferably an alkyl group, having 1 to 24, preferably from 1 to 18, more preferably 1 to 8, carbon atoms. The repeating unit (1) can be prepared from a monomer represented by the following formula (i), hereinafter referred to as monomer (i).

(i)

In the formula (i), $R^1$ and $R^2$ are as defined above.

Preferably, the repeating unit (1) is contained in the copolymer in an amount of from 25 to 75 wt %, more preferably from 30 to 60 wt %, based on weight of the copolymer. If the content of the repeating unit (1) is outside the aforesaid range, desired thickening capability may not be attained.

In the repeating unit represented by the above formula (2), hereinafter referred to as the repeating unit (2), $R^1$ is as defied above and preferably is a hydrogen atom or a methyl group. X is a hydrogen atom, an alkali metal atom, an organic ammonium ion or ammonium ion. When the present composition is used as a thickener, at least a part of, preferably all of, X is an alkali metal cation, organic ammonium ion or ammonium ion. Preferred examples of X include sodium, potassium, ammonium, alkanol ammonium, particularly, ethanol ammonium ion.

The repeating unit (2) is contained in the copolymer in an amount of from 20 to 60 wt %, preferably from 30 to 55 wt %, based on weight of the copolymer. With the repeating unit (2) less than the aforesaid lower limit, desired thickening capability may not be attained. On the other hand, with the repeating unit (2) more than the aforesaid upper limit, the thickening capability will not be proportionally increased.

The repeating unit (2) with X being a hydrogen atom can be derived from the monomer represented by the following formula (ii), hereinafter referred to as monomer (ii), wherein $R^1$ is as defined above.

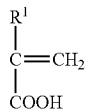
(ii)

By reacting a polymer obtained with an alkaline such as sodium hydroxide, potassium hydroxide, ammonia water, or an alkanol amine, for example, ethanolamine, the repeating unit (2) with X being a cation such as sodium ion can be obtained.

In the repeating unit represented by the above formula (3), hereinafter referred to as the repeating unit (3), $R^1$ is as defined above and preferably is a hydrogen atom or a methyl group. $R^3$ is a divalent hydrocarbon group having 1 to 4 carbon atoms, preferably an alkylene group having 1 to 4 carbon atoms, more preferably, a propylene group. $R^4$, which may be the same as or different from each other, is an aliphatic hydrocarbon group having 1 to 6 carbon atoms, preferably a methyl group, or a phenyl group. In the formula (3), m is an integer of from 0 to 500, preferably from 0 to 300, more preferably from 0 to 250. It should be noted that the number of the siloxane unit, m, is distributed as in an ordinary polysiloxane. Some repeating unit (3) may have the siloxane units more than the aforesaid upper limit, but averaged number falls within the aforesaid range. A repeating unit with an averaged m being larger than the aforesaid upper limit is difficult to prepare. In the formula (3), n is an integer of from 1 to 3. Particularly, preferred repeating unit (3) is the one with n being 1 and m being an integer of from 10 to 250 on average.

Preferred examples of the repeating unit (3) are as shown below.

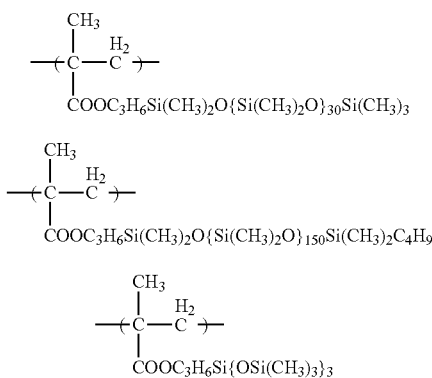

The repeating unit (3) is contained in the copolymer preferably in an amount of from 2 to 35 wt %, more preferably from 3 to 30 wt %, most preferably from 3 to 25 wt %. With the repeating unit (3) less than the aforesaid lower limit, desired capability of emulsifying silicone oil into O/W emulsion may not be attained. With the repeating unit (3) more than the aforesaid upper limit, emulsifying capability will not be proportionally increased.

The repeating unit (3) can be derived from the monomer or a macromer, which is an oligomeric or polymeric monomer, represented by the following formula (iii), hereinafter referred to as monomer (iii).

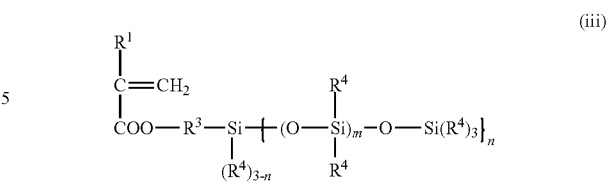

In the formula (iii), $R^1$, $R^3$, $R^4$, and m are as defined above.

The aforesaid repeating units (1), (2) and (3) are bonded blockwise or randomly, preferably randomly, to form copolymer main chains. The main chains are crosslinked by a compound or oligomer each having 2 to 6 (meth)acrylic groups per molecule, hereinafter referred to as crosslinking agent. Examples of the crosslinking agent include tris(2-(meth) acryloyloxyethyl) isocyanurate, trimethylolpropane tri (meth)acrylate, 1,4-butanediol(meth)acrylate, 1,6-hexanediol(meth)acrylate, 1,9-nonanediol(meth)acrylate, pentaerythritol tri(meth)acrylate, pentaerythritol tetra(meth) acrylate, dipentaerythritolhexa(meth)acrylate, tri(meth)acrylate of an EO adducts of trimethylolpropane, tri(meth)acrylate of a PO adducts of glycerin, glycerin di(meth)acrylate, glycerin tri(meth)acrylate, polyoxyalkylene di(meth)acrylate of the following formula (4), polyorganosiloxane compound of the following formula (5), polyorganosiloxane compound of the following formula (6), and polyorganosiloxane compound of the following formula (7).

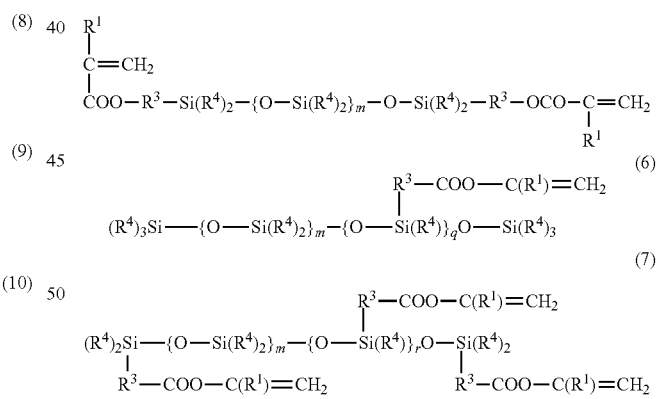

In the formulas (4) to (7), $R^1$, $R^3$, $R^4$ and m are as defined above. In the formula (4), $R^5$ is a divalent hydrocarbon group, preferably an alkylene group, having 1 to 4 carbon atoms, $R^6$ is a hydrogen atom or a methyl group, and p is an integer of from 1 to 50, preferably from 5 to 30. If p exceeds 50, a reaction rate of crosslinking may be low. In the formula (6), q is an integer of from 2 to 6. In the formula (7), r is an integer of from 0 to 4.

Preferred are tris(2-(meth)acryloyloxyethyl)isocyanurate, trimethylolpropane tri(meth)acrylate, polyoxyalkylene di(meth)acrylate of the formula (4), and polyorganosiloxane compound of the formula (5).

The crosslinking agent is used in an amount of from 0.05 to 4 wt %, preferably from 0.05 to 3.4 wt %, more preferably from 0.1 to 2 wt %, based on weight of the copolymer. If it is used in an amount below the aforesaid lower limit, a copolymer will be obtained which has a lower degree of crosslinkage, resulting in lower thickening capability. If it is used in an amount above the aforesaid upper limit, a copolymer will be obtained which may have too high degree of crosslinkage to have a desired thickening capability.

In the present invention, the copolymer can be prepared by subjecting a mixture of the aforesaid monomers (i), (ii), (iii) in such a mixing ratio to provide the aforesaid contents of the repeating unit, and the aforesaid amount of the crosslinking agent to a polymerization reaction in the presence of a radical polymerization initiator such as benzoylperoxide, lauroylperoxide, azobisisobutyronitrile.

In addition to the above monomers (i), (ii) and (iii), other monomers may be used in such an amount that they do not adversely affect the property of the copolymer. Examples of the monomer include nonionic monomers such as cyclohexyl (meth)acrylate, hydroxyethyl(meth)acrylate, polyoxyalkylene mono(meth)acrylate, (poly)glycerin mono(meth)acrylate, acrylamide, vinylpyrrolidone, and styrene; cationic monomers such as (meth)acryloyloxyhydroxypropyltrimethylammonium chloride, dimethylaminoethyl(meth)acrylate, diethylaminoethyl(meth)acrylate, and dimethylaminopropyl(meth)acrylate; anionic monomers such as maleic acid, maleic acid anhydride, itaconic acid, fumaric acid, crotonic acid, 2-methacryloyloxyethyl phosphate, 2-methacryloyloxypropyl phosphate, and 3-chloro-2-phosphoxypropyl (meth)acrylate.

Polymerization reaction can be performed in a known method. Preferably, emulsion polymerization method is employed. That is, the monomers and the crosslinking agent are emulsified in water to prepare an emulsion having a total solid content of from 10 to 50 wt %, to which an polymerization initiator is added, and then subjected to polymerization at a temperature of from 40 to 60° C. for 2 to 5 hours. In the emulsifying step, an anionic surfactant such as N-lauroylmethyl taurine sodium salt, or a nonionic surfactant having an HLB of from 11 to 18 may be used. An emulsion or dispersion of a copolymer obtained can be used without further treatment, or at least part of the carboxyl groups of the copolymer may be neutralized with an inorganic base such as sodium hydroxide or potassium hydroxide, or an organic acid such as triethanol amine. Alternatively, the copolymer can be isolated by spray-drying the dispersion.

Alternatively, the polymerization may be performed in an organic solvent, for example, aliphatice solvents such as pentane, hexane, decane, dodecane, hexadecane, and octadecane; aromatic solvents such as benzene, toluene, and xylene; alcohols such as methanol, ethanol, propanol, butanol, hexaneol, and dodecanol; halogenated solvents such as chloroform and carbon tetrachloride; or ketone solvents such as acetone and methyl ethyl ketone.

The present composition contains the aforesaid copolymer in an amount of from 0.5 to 50 wt %, preferably from 10 to 50 wt % in water. The composition is suitable as a thickener for aqueous cosmetics. The composition is also suitable as an emulsifier for silicone oils to form finely textured emulsion. Particularly, the composition is suitable for preparing an oil-in-water type emulsion, which is advantageously used to prepare cosmetics that do not cause sticky or greasy touch. The cosmetics also do not leave sticky touch on the skin after they are dried on the skin. Preferably, the composition of the present invention is provided in the form of an oil-in-water type emulsion and diluted with an appropriate amount of water depending on cosmetics to be prepared. Alternatively, water or organic solvent is removed from the composition to form powder which is then incorporated in cosmetics as a thickener or an emulsifier.

The present invention provides a cosmetic comprising the present composition. The cosmetic is aqueous cosmetics, i.e., cosmetics containing water, to be applied to the skin or hair. Examples of the cosmetic include skincare cosmetics, hair cosmetics, antiperspirant, makeup cosmetics, and UV-ray protective cosmetics. Examples of the skincare cosmetics include basic cosmetics such as milky lotion, cream, lotion, calamine lotion, cleansing, pack, oil liquid, massage cream, soap, deodorant lotion, hand cream, lip cream, after shave lotion, and pre-shave lotion. Examples of the hair cosmetics include shampoo, rinse, conditioner, treatment, hair color, hair tonic, and setting agent. Examples of UV-ray protective cosmetics include sun screen agent and sun tan agents. Examples of the makeup cosmetics include make up base, liquid foundation, eye shadow, mascara, eye liner, eyebrow, and lipstick.

Further, the present cosmetic may be in various forms such as liquid, emulsion, solid, paste, gel, and mousse. Preferably, the cosmetic is an O/W-type cream, foundation, shampoo or rinse.

The cosmetic contains the composition of the present invention in an amount, as solid, of from 0.1 to 10.0 wt %, preferably from 0.2 to 8.0 wt %, more preferably from 0.5 to 5.0 wt %, based on total weight of the cosmetic. Here, the "solid" may include water which cannot be removed by ordinary methods.

The cosmetic of the present invention can contain various components such as (E) an unctuous agent and (F) an alcohol having 2 to 10 carbon atoms, as will be explained below.

Any unctuous agent (E), solid, semisolid or liquid at room temperature, which is commonly used for cosmetics, can be used. Preferably, a part of or all of the unctuous agent (E) is liquid at room temperature. Examples of the unctuous agent (E) include natural animal or plant oils, semisynthetic oils, hydrocarbon oils, higher fatty acids, higher alcohols, ester oils, glyceride oils, silicone oils and fluorine-containing oils.

Examples of the natural animal or plant oils and semisynthetic oils include avocado oil, linseed oil, almond oil, Ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, camellia kissi seed oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein POE means polyoxyethylene.

Examples of the hydrocarbon oils include ozokerite, squalane, squalene, ceresin, paraffin, paraffin wax, liquid paraffin, pristane, polyisobutylene, microcrystalline wax, vaseline and higher fatty acids, e.g., lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether(batyl alcohol), and monooleyl glyceryl ether(cerakyl alcohol).

Examples of the ester oils include diisobutyl adipate, 2-hexyldecyl adipate, di-2-heptylundecyl adipate, N-alkyl glycol monoisostearate, isocetyl isostearate, trimethylolpropane triisostearate, isononyl isononanate, isotridecyl isononanate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate; and glyceride oils, e.g., acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

Examples of the silicone oils include organopolysiloxanes having a low or high viscosity, such as dimethylpolysiloxane, methylphenylpolysiloxane, methylhydrogenpolysiloxane and dimethylsiloxane-methylphenylsiloxane copolymer; cyclosiloxanes, such as octamethylcyclotetrasiloxane, decamethylcyclopentasiloxane, dodecamethylcyclohexasiloxane, tetramethyltetrahydrogencyclotetrasiloxane and tetramethyl-tetraphenylcyclotetrasiloxane, tetramethyltetretrifluoropropyl cyclotetrasiloxane pentamethyltrifluoropropyl cyclopentasiloxane; silicone rubbers, such as gummy dimethylpolysiloxanes and gummy dimethylsiloxane-methylphenylsiloxane copolymers having high polymerization degrees; solutions of silicone rubbers in cyclosiloxane, trimethylsiloxysilicate, solutions of trimethylsiloxysilicate in cyclosiloxane, higher alkyl-modified silicones such as stearoxysilicone, alkyl-modified silicones, amino-modified silicones, fluorine-modified silicones, silicone resin and silicone resin solutions.

Examples of the fluorine-containing oils include perfluoropolyether, perfluorodecalin, perfluorooctane, pitch fluoride, and fluoroalcohol, and a mixture thereof.

A content of the unctuous agent (E) in the cosmetic, though it varies depending on a form of the cosmetics, preferably ranges from 1.0 to 80.0 wt %, more preferably from 1.0 to 50.0 wt %. If unctuous agent (E) is contained in an amount less than the aforesaid lower limit, effect of the unctuous agent (E) may not be exerted. A cosmetic containing the unctuous agent (E) more than the aforesaid upper limit may be greasy or sticky.

The present composition may contain (F) an alcohol having 2 to 10 carbon atoms, preferably, water-soluble mono- or polyhydric alcohol. A content of the component (F) can be adjusted according to a form of cosmetics, but preferably ranges from 0.1 to 50.0 wt %. If the content is below the aforesaid lower limit, desired antibacterial or antifungal effect may not be attained. If the content is above the aforesaid upper limit, cosmetics may be sticky.

Examples of the component (F) include ethanol and isopropanol; sugar alcohols such as sorbitol and maltose; sterols such as cholesterol, sitosterol, phytosterol, and lanosterol; and polyhydric alcohol such as glucose, butylene glycol, propylene glycol, dibuthylene glycol, and pentylene glycol.

The cosmetic of the present invention may contain (G) a water-soluble or water-swelling polymer. Examples of such polymer include plant polymers such as gum Arabic, tragacanth gum, arabinogalactan, guar gum, karaya gum, carrageenan, pectin, agar, quince seed (i.e., marmelo), starch from rice, corn, potato or wheat, algae colloid, trant gum, and locust bean gum (carob gum); bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyoxyethylene/polyoxypropylene copolymers; acrylic polymers such as sodium polyacrylate, polyethyl acrylate, and polyacrylamide; other synthetic water-soluble polymers such as polyethyleneimine and cationic polymers; and inorganic water-soluble polymers such as, bentonite, aluminum magnesium silicate, montmorrilonite, beidellite, nontronite, saponite, hectorite, and silicic anhydride.

The component (G) is contained in the cosmetic in an amount of from 0.01 to 25.0 wt %, based on total weight of the cosmetic. If it is contained in an amount less than the aforesaid lower limit, satisfactory film forming property may not be attained. A cosmetic containing the component (G) more than the aforesaid upper limit may be sticky.

The present cosmetic may further contain components conventionally used in cosmetics such as (H) powder, (I) a surfactant, (J) a crosslinked organopolysiloxane, (L) a silicone resin which is gummy or solid at room temperature, and (M) an UV-ray protective agent.

As the powder (H), any powder which are commonly used in cosmetics may be used, regardless of the shape such as spherical, spindle forms, acicular, and plate-like; particle size such as fume size, fine particles and pigment grade; and particle structure such as porous and non-porous. Examples of the powder include inorganic powder, organic powder, metal salt powder of surface active agent, colored pigments, pearl pigments, metallic powder pigments, and natural colors and the like.

Examples of the inorganic powder include inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectoliter, zeolite, ceramics powder, calcium secondary phosphate, alumina, aluminum hydroxide, boron nitride, and silica.

Examples of the organic powder include polyamide powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, powder of nylon such as Nylon 12 and Nylon 6, crosslinked dimethylsilicone elastomer powder as described in Japanese Patent Application Laid-Open No. 3-93834, polymethylsylsesquioxane spherical powder as described in Japanese Patent Application Laid-Open No. 3-47848, silicone elastomer spherical powder coated with polymethylsylsesquioxane as described in Japanese Patent Application Laid-Open No. 7-196815, powder of styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcrystalline fiber, starch powder, and lauroyl lysine.

Examples of the powder of metal salts of surfactants, i.e. metal soaps, include zinc stearate, aluminum stearate, calcium stearate, magnesium stearate, zinc myristate, magnesium myristate, zinc cetyl phosphate, calcium cetyl phosphate, and zinc sodium cetyl phosphate.

Examples of the colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder, composite thereof.

Examples of the pearl pigments include titanium dioxide-coated mica, bismuth oxychloride, titanium dioxide-coated bismuth oxychloride, titanium dioxide-coated talc, fish scales, and titanium dioxide-coated colored mica; metallic powder pigments such as aluminum powder, copper powder and stainless steel powder Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin.

The powder may be in the form of composite or may be treated with silicone oil, fluorine compound, or surfactant to the extent not to adversely affect the present cosmetics. For example, the powder may or may not be treated beforehand with fluorine compound, silicone resin, silane coupling agent, titanium coupling agent, unctuous agent, N-acyl lysine, polyacrylic acid, metal surfactant, amino acid, inorganic compound; treatment of pendants; plasma treatment, or mechanochemical treatment. Two or more of the treatment may be employed.

Preferably, silicone elastomer spherical powder, polyethylene powder, polypropylene powder, polytetrafluoroethylene powder, polymethylsilsesquioxane spherical powder, silicone elastomer spherical powder coated with polymethylsilsesquioxane, and polyurethane powder are used to attain good stability with time and feel to the touch.

A content of the powder (H) in the cosmetic varies depending on the form of the cosmetics. Generally, the content ranges from 0.1 to 50 wt %, preferably from 0.5 to 30 wt %, based on a total weight of the cosmetics.

The surfactant (I) include anionic, cationic, nonionic or amphoteric surfactants, among which appropriate one is selected according to the cosmetic. For example, a nonionic surfactant is preferably used for skin cream, an anionic surfactant or betaine surfactant is preferably used for shampoo, and cationic surfactant is preferably used for rinse.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified linear or branched organopolysiloxane (Japanese Patent No. 2137062, Japanese Patent Application Laid-Open No. 7-330907), polyglycerin-modified linear or branched organopolysiloxane (Publication of Examined Japanese Patent Application No. 62-34039, Japanese Patent No. 2613124, Japanese Patent No. 2844453, Japanese Patent Application Laid-Open No. 2002-179798), polyoxyalkylene/alkyl-co-modified organopolysiloxane (Japanese Patent Application Laid-Open No. 61-90732, Japanese Patent Application Laid-Open No. 9-59386), alkanolamide, sugar ethers, and sugar amides. Preferably, the surfactant (I) is selected from the group consisting of a polyoxyalkylene-modified linear or branched organopolysiloxane, a polyglycerin-modified linear or branched organopolysiloxane and alkyl-comodified derivative thereof.

Examples of the anionic surfactants include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate salts of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil salfate, alkyl phosphate salts, ether phosphate salts, alkylallylether phosphate salts, amide phosphate salts, and N-acylamino surfactants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the amphoteric surfactants include betaine, aminocarboxylates, and imidazoline derivatives. The surfactant (I) is contained in the cosmetic preferably in an amount of from 0.1 to 20 wt %, more preferably from 0.5 to 10 wt %, based on total weight of the cosmetic.

The cosmetics of the present invention may contain (J) a composition consisting of a crosslinked organopolysiloxane and liquid oil. The crosslinked organopolysiloxane can be obtained by reacting an alkylhydrogenpolysiloxane with a crosslinking agent having reactive vinyl group. Examples of the alkylhydrogenpolysiloxane include linear and partly branched methylhydrogenpolysiloxanes and methylhydrogenpolysiloxane having $C_{6-20}$ alkyl chains grafts. The alkylhydrogenpolysiloxane should have at least two, on average, hydrogen atoms per molecule. Examples of the crosslinking agent include methylvinylpolysiloxane and alkenyldiene which have at least two vinyl groups per molecule. Examples of the crosslinked organopolysiloxane are those described in Japanese Patent No. 1925781, Japanese Patent No. 1932769, and WO 03-24413. The crosslinked organopolysiloxane is swollen with the liquid oil such as a silicone oil having a viscosity of from 0.65 mm$^2$/sec (25° C.) to 100.0 mm$^2$/sec (25° C.), liquid paraffin, squalane, hydrocarbon oil such as isododecane, glyceride oil such as trioctanoyne, and ester oils.

The crosslinked organopolysiloxane swollen with oil (J) is contained in the cosmetic in an amount of from 0.5 to 60 wt %, preferably from 2 to 50 wt %, more preferably from 3 to 40 wt %, based on total weight of the cosmetics, though the content can be varied depending on a type and content of the oil.

The cosmetic of the present invention may contain (K) a composition consisting of a crosslinked organopolysiloxane having a polyether and/or polyglycerin moiety and a liquid oil. The crosslinked organopolysiloxane can be obtained by reacting an alkylhydrogenpolysiloxane with a crosslinking agent having reactive vinyl groups. Examples of the alkylhydrogenpolysiloxane include methylhydrogenpolysiloxanes grafted with polyoxyethylene chains and methylhydrogenpolysiloxane grafted with polyglycerin chains. The alkylhydrogenpolysiloxane should have at least two, on average, hydrogen atoms per molecule. The crosslinked organopolysiloxane is swollen with liquid oil such as silicone oil having a viscosity of from 0.65 mm$^2$/sec (25° C.) to 100.0 mm$^2$/sec (25° C.), liquid paraffin, squalane, hydrocarbon oil such as isododecane, glyceride oil such as trioctanoyne, and ester oils.

Examples of the crosslinking agent include methylvinylpolysiloxane, α,ω-alkenyldiene, glycerin triallyl ether, polyoxyalkynylated glycerin trially ether, trimethylolpropane trially ether, polyoxyalkynylated trimethylolpropane trially ether. The crosslinked organopolysiloxane preferably has at least one moiety selected from the group consisting of polyoxyalkylene group, polyglycerin residue, alkyl group, alkenyl group, aryl group, and fluoroalkyl group. Preferred examples of the composition (K) are those described in Japanese Patent No. 2631772, Japanese Patent Application Laid-Open No. 9-136813, Japanese Patent Application Laid-Open No. 2001-342255, and WO 03/20828.

The crosslinked organopolysiloxane swollen with oil (K) is contained in the present cosmetic in an amount of from 0.5 to 60 wt %, preferably from 2 to 50 wt %, more preferably from 3 to 40 wt %, based on total weight of the cosmetic, though the content can be varied depending on a type and content of the oil.

The present cosmetic may contain (L) a silicone resin selected from the group consisting of silicone network compounds containing $SiO_2$ units and/or $RSiO_{1.5}$, wherein R is an alkyl group, and a linear acryl/silicone graft- or block-copolymer. The linear acryl/silicone graft- or block-copolymer may contain at least one moiety selected from the group consisting of pyrrolidone moiety, long-chain alkyl moiety, polyoxyalkylene moiety, fluoroalkyl moiety, amino moiety and anionic moiety such as carboxyl group.

The silicone network compounds which are combinations of M,T,D, and Q units such as MQ, MDQ, MTQ, MDTQ, TD, TQ, TDQ resin, wherein M is $R_3SiO_{0.5}$ unit, D is a $R_2SiO$ unit, T is a $RSiO_{1.5}$ unit, and Q is $SiO_2$ unit.

The silicone resin such as the acryl/silicone resin or the silicone network compound is incorporated in the cosmetic in the form of resinous solid or in the form of a solution dissolved in silicone oil having low-viscosity or other kind of solvent. The silicone resin is contained in the cosmetic in an amount of, as solid, preferably from 0.1 to 20 wt %, more preferably from 1 to 10 wt %, based on total weight of the cosmetic.

Examples of the UV-ray protective agent (M) include those of the aforesaid inorganic pigments and metal powder which can scatter UV-ray and organic UV-ray absorber. The UV-ray scattering inorganic pigments or metal powder are preferably incorporated in the cosmetics in the form of dispersion in the unctuous agent. Examples of the dispersion of UV-ray scattering titanium oxide in decamethylcyclopentasiloxane (D5) are SPD-T1, T2, T1S, T1V, T3V, and T5, all from Shin-Etsu Chemical Co. Ltd. Examples of the dispersion of UV-ray scattering zinc oxide in decamethylcyclopentasiloxane (D5) are SPD-Z1, Z2, Z3, Z1S, Z3S, and Z5, all from Shin-Etsu Chemical Co. Ltd. In place of D5, other unctuous agents such as M3T, M4Q, volatile or non-volatile hydrocarbon oils can be used.

Examples of the organic ultraviolet light absorbents include benzoic acid derivatives such as p-aminobenzoic acid, ethyl p-aminobenzoate, and glyceryl p-aminobenzoate, p-dimethylaminoamyl bezoate, p-dimethylaminooctyl bezoate, 4-[N,N-di(2-hydroxypropyl)amino]ethyl benzoate; salicylic acid derivatives such as methyl salicylate, ethylene glycol salicylate, phenyl salicylate, octyl salicylate, benzyl salicylate, p-tert-phenyl butylphenyl salicylate, and homomentyl salicylate; cinnamic acid derivatives such as benzyl cinnamate, 2-ethoxyethyl-p-methoxy cinnamate, and glyceryl mono-2-ethylhexanoyl-di-p-methoxy cinnamate; urocanic acid and, ethyl urocanate; benzophenone derivatives such as hydroxymethoxy benzophenone, hydroxymethoxy benzophenone sulfonic acid, sodium hydroxymethoxy benzophenone sulfonate, dihydroxymethoxy benzophenone, sodium dihydroxydimethoxy benzophenone sulfonate, 2,4-dihydroxy benzophenone, and tetrahydroxy benzophenone; dibenzoyl methane derivative such as 4-tert-butyl-4'-methoxy-dibenzoyl methane; anthranilic acid derivatives such as methyl anthranilate; benzotriazol derivative such as 2-(2-hydroxy-5-methylphenyl)benzotriazol; and higher molecular weight derivatives thereof, and silane or siloxane derivative thereof.

A content of the UV-ray protective agent (M) ranges preferably from 0.1 to 20 wt %, more preferably from 1 to 10 wt %, based on total weight of the cosmetic. Particularly preferred UV-ray protective agents are 2-ethylhexyl p-methoxy cinnamate, and 4-t-butyl-4'-methoxy-dibenzoylmethane.

The UV-ray protective agent (M) may be encapsulated in polymer powder. The polymer powder may or may not be hollow. Preferably, a diameter of primary particle of the powder ranges from 0.1 to 50 μm with a broad or sharp diameter distribution. Examples of the polymer include acrylic, methacrylic, polystyrene, polyurethane, polyethylene, polypropylene, polyethylene terephthalate, silicone, polyamide, and acrylamide resins. Preferably, 0.1 to 30 wt % of the organic UV-ray protective agent, particularly 4-t-butyl-4'-methoxy dibenzoylmethane, which is a UV-A absorber, is contained in the polymer powder.

In the cosmetic of the present invention, other components that are commonly used in cosmetics can be incorporated in an amount not to adversely affect the cosmetic. Examples of the components include film forming agent, oil-soluble gelling agents, clay minerals modified with organic compounds, resins, moisture retention agents, antiseptics, anti-microbial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, and clathrate compounds.

Examples of the oil-soluble gelling agent include metal soaps, such as aluminum stearate, magnesium stearate and zinc myristate; amino acid derivatives, such as N-lauroyl-L-glutamic acid and α, γ-di-n-butylamine; dextrin fatty acid esters, such as dextrin palmitic acid ester, dextrin stearic acid ester and dextrin 2-ethylhexaminic acid palmitic acid ester; inulin fatty acid esters such as fructooligostearate; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay. A mixture of two or more of these can be incorporated in an oil phase of the cosmetic.

Examples of a moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of the antiseptics include alkyl p-oxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide and phenoxyethanol.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediamine tetraacetate, sodium polyphosphate, sodium metaphosphate and phosphoric acid examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents include placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

EXAMPLES

The present invention will be explained with reference to the following examples, but not limited thereto.

Examples 1-5 and Referential Examples 1-6

In a homomixer, were mixed ethyl acrylate and/or stearyl methacrylate to derive the repeating unit (1), methacrylic acid to derive the repeating unit (2), an organopolysiloxane macromer to derive the repeating unit (3), a crosslinking agent, ion-exchanged water (5a), and an emulsifier according to the formulations as shown in Table 1. In a reactor, ion-exchanged water (5b) in an amount as shown in Table 1 was placed, to which the above mixture and a catalyst were added and subjected to a reaction at a temperature of 50° C. for 3 hours to prepare a copolymer dispersed in ion-exchanged water. To the dispersion, ion-exchanged water was added so as to make a concentration of the copolymer 1 wt %. Subsequently, the dispersion was neutralized by adding dropwise a 10% aqueous solution of sodium hydroxide in an amount of theoretical equivalent to methacrylic acid fed. The dispersion thus obtained is hereinafter referred to as neutralized dispersion.

The neutralized dispersion was evaluated according to the following methods.

Viscosity

Viscosity of the neutralized dispersion was measured with a rotational viscometer at 25° C.

Sense of the Touch after Dried

About 0.5 g of the neutralized dispersion was applied to the skin of an arm. The applied dispersion was air-dried and then touched by a finger. The sense of the touch was rated according to the following criteria.

A: Smooth to the touch with little stickiness

B: A little sticky

C: Very sticky

Average Particle Size of Oil Phase in Emulsion

Seventy five parts by weight of the neutralized dispersion was mixed with 25 parts by weight of dimethylpolysiloxane having a viscosity of 6 mm$^2$/s with a disperser mixer at 3,000 rpm for 5 minutes. Particle size of an oil phase of the O/W emulsion thus obtained was measured with a Coulter counter.

The results are as shown in Table 1, wherein "Ex." stands for Example and "Ref.Ex." stands for Referential Example.

TABLE 1

| | | | Ex. 1 | Ex. 2 | Ex. 3 | Ex. 4 | Ex. 5 | Ref. Ex. 1 |
|---|---|---|---|---|---|---|---|---|
| Component | 1a | Ethyl acrylate | 50 | 37 | 50 | 56.5 | 31.5 | 49.98 |
| | 1b | Stearyl methacrylate | 0 | 3 | 0 | 3 | 3 | 0 |
| | 2 | Methacrylic acid | 44.8 | 39.8 | 43 | 30 | 55 | 45 |
| | 3a | macromer*[1] | 5 | 20 | 5 | 10 | 10 | 5 |
| | 4a | crosslinking agent*[2] | 0.2 | 0.2 | 2 | 0.5 | 0.5 | 0.02 |
| | 5a | Ion exchanged water | 59.1 | 80.2 | 59.1 | 80.2 | 80.2 | 59.1 |
| | 6a | Emulsifier*[3] | 0.7 | 0.6 | 0.7 | 0.6 | 0.6 | 0.7 |
| | 6b | Emulsifier*[4] | 0.5 | 0.4 | 0.5 | 0.4 | 0.4 | 0.5 |
| | 6c | Emulsifier*[5] | 6.8 | 5.6 | 6.8 | 5.6 | 5.6 | 6.8 |
| | 6d | Emulsifier*[6] | 0.5 | 0.4 | 0.5 | 0.4 | 0.4 | 0.5 |
| | 5b | Ion exchanged water | 348.3 | 530.3 | 348.3 | 530.3 | 530.3 | 348.3 |
| | 7a | Catalyst*[7] | 0.001 | 0.001 | 0.001 | 0.001 | 0.001 | 0.001 |
| | 7b | Catalyst*[8] | 0.04 | 0.05 | 0.04 | 0.05 | 0.05 | 0.04 |
| | 7c | Catalyst*[9] | 0.04 | 0.05 | 0.04 | 0.05 | 0.05 | 0.04 |
| Viscosity (mPa·s) | | | 9500 | 7600 | 5200 | 4980 | 7450 | 820 |
| Sense of touch after dried | | | B | A | B | A | B | B |
| Average particle size of oil phase (μm) | | | 4.5 | 3.2 | 6.5 | 5.6 | 5.1 | 18.5 |

| | | | Ref. Ex. 2 | Ref. Ex. 3 | Ref. Ex. 4 | Ref. Ex. 5 | Ref. Ex. 6 |
|---|---|---|---|---|---|---|---|
| Component | 1a | Ethyl acrylate | 45 | 54 | 15 | 73.8 | 26.8 |
| | 1b | Stearyl methacrylate | 0 | 0 | 0 | 3 | 3 |
| | 2 | Methacrylic acid | 45 | 44.8 | 44.8 | 18 | 65 |
| | 3a | macromer*[1] | 5 | 1 | 40 | 5 | 5 |
| | 4a | crosslinking agent*[2] | 5 | 0.2 | 0.2 | 0.2 | 0.2 |
| | 5a | Ion exchanged water | 59.1 | 59.1 | 59.1 | 80.2 | 80.2 |
| | 6a | Emulsifier*[3] | 0.7 | 0.7 | 0.7 | 0.6 | 0.6 |
| | 6b | Emulsifier*[4] | 0.5 | 0.5 | 0.5 | 0.4 | 0.4 |
| | 6c | Emulsifier*[5] | 6.8 | 6.8 | 6.8 | 5.6 | 5.6 |
| | 6d | Emulsifier*[6] | 0.5 | 0.5 | 0.5 | 0.4 | 0.4 |
| | 5b | Ion exchanged water | 348.3 | 348.3 | 348.3 | 530.3 | 530.3 |
| | 7a | Catalyst*[7] | 0.001 | 0.001 | 0.001 | 0.001 | 0.001 |
| | 7b | Catalyst*[8] | 0.04 | 0.04 | 0.04 | 0.05 | 0.05 |
| | 7c | Catalyst*[9] | 0.04 | 0.04 | 0.04 | 0.05 | 0.05 |
| Viscosity (mPa·s) | | | 680 | 10500 | 1230 | 910 | 2100 |
| Sense of touch after dried | | | C | C | A | C | C |
| Average particle size of oil phase (μm) | | | 25.6 | 12.4 | 12.4 | 14.8 | 13.2 |

*[1]Organopolysiloxane represented by the formula (8) $CH_2=C(CH_3)COOC_3H_6Si(CH_3)_2O\{Si(CH_3)_2O\}_{30}Si(CH_3)_3$ (8)
*[2]Tris(2-acryloyloxyethyl) isocyanurate
*[3]Sodium N-lauroylmethyl taurine
*[4]Polyethylene glycol monooleate (HLB = 13.7)
*[5]Polyoxyethylene sorbitan monostearate (HLB = 14.9)
*[6]Polyoxyethylene coconut oil fatty acid sorbitan ester (HLB = 16.7)
*[7]ferrous sulfate
*[8]t-butylhydroperoxide
*[9]sodium formaldehyde sulfoxylate Examples 6-9

In a homomixer, were mixed ethyl acrylate and/or methyl methacrylate to derive the repeating unit (1), methacrylic acid to derive the repeating unit (2), an organopolysiloxane macromer to derive the repeating unit (3), a crosslinking agent, ion-exchanged water (5a), and an emulsifier according to the formulations as shown in Table 1. In a reactor, ion-exchanged water (5b) in an amount as shown in Table 1 was placed, to which the above mixture and a catalyst were added and subjected to a reaction at a temperature of 50° C. for 3 hours to prepare a copolymer dispersed in ion-exchanged water. To the dispersion, ion-exchanged water was added so as to make a concentration of the copolymer 1 wt %. Subsequently, the dispersion was neutralized to pH 7 by adding dropwise a 10% aqueous solution of sodium hydroxide. The dispersion thus obtained, hereinafter referred to as neutralized dispersion, were evaluated according to the aforesaid methods. The results are as shown in Table 2.

TABLE 2

| Component | | | Ex. 6 | Ex. 7 | Ex. 8 | Ex. 9 |
|---|---|---|---|---|---|---|
| Component | 1a | Ethyl acrylate | 39.8 | 34.8 | 34.8 | 34.8 |
| | 1c | Methyl acrylate | 0 | 20 | 20 | 15 |
| | 2 | Methacrylic acid | 40 | 40 | 40 | 40 |
| | 3b | macromer*[10] | 20 | 0 | 5 | 5 |
| | 3b | macromer*[11] | 0 | 5 | 0 | 5 |
| | 4a | crosslinking agent*[12] | 0.2 | 0 | 0 | 0.1 |
| | 4a | crosslinking agent*[13] | 0 | 0.2 | 0 | 0.1 |
| | 4a | crosslinking agent*[14] | 0 | 0 | 0.2 | 0 |
| | 5a | Ion exchanged water | 70.6 | 59.1 | 59.1 | 59.1 |
| | 6a | Emulsifier*[3] | 0.6 | 1 | 0.7 | 0.7 |
| | 6b | Emulsifier*[4] | 0.4 | 0 | 0.5 | 0.5 |
| | 6c | Emulsifier*[5] | 5.6 | 0 | 6.8 | 6.8 |
| | 6d | Emulsifier*[6] | 0.4 | 0 | 0.5 | 0.5 |
| | 6f | Emulsifier*[6] | 0 | 5 | 0.2 | 0.2 |
| | 5b | Ion exchanged water | 346.7 | 348.3 | 348.3 | 348.3 |
| | 7a | Catalyst*[7] | 0.001 | 0 | 0 | 0.001 |
| | 7b | Catalyst*[8] | 0.04 | 0.05 | 0.04 | 0.05 |
| | 7c | Catalyst*[16] | 0.04 | 0 | 0.02 | 0.05 |
| | 7e | Catalyst*[17] | 0 | 0.05 | 0.02 | 0 |
| Viscosity (mPa · s) | | | 8500 | 8000 | 6200 | 5080 |
| Sense of touch after dried | | | A | B | B | A |
| Average particle size of oil phase (μm) | | | 5.9 | 4.8 | 5.1 | 6.0 |

*[10] Organopolysiloxane represented by the following formula (9) $CH_2=C(CH_3)COOC_3H_6Si(CH_3)_2O\{Si(CH_3)_2O\}_{150}Si(CH_3)_2C_4H_9$ (9)
*[11] Organopolysiloxane represented by the following formula (10) $CH_2=C(CH_3)COOC_3H_6Si\{OSi(CH_3)_3\}_3$ (10)
*[12] Trimethylolpropane triacrylate
*[13] Organopolysiloxane represented by the following formula (11) $CH_2=C(CH_3)COOC_3H_6Si(CH_3)_2O\{Si(CH_3)_2O\}_{50}Si(CH_3)_2C_3H_6OCOC(CH_3)=CH_2$ (11)
*[14] Polyoxyethylene dimethacrylate (EO = 10 moles)
*[15] Polyoxyethylene lauryl ether (EO = 17 moles)
*[16] L-ascorbic acid
*[17] Sodium L-ascorbate Comparative Example 1

A 30 wt % aqueous dispersion of a copolymer, ASE-60, ex Japan Acryl Chemical Co., was diluted with ion-exchanged water to 1 wt % dispersion which was then neutralized with a 10% aqueous solution of sodium hydroxide. The neutralized dispersion thus obtained was evaluated according to the aforesaid methods. The viscosity measured was 8,000 mPa·s, the touch after dried was very sticky, and the average particle size was 11.0 μm.

As is found from Tables 1 and 2, the compositions of Examples showed satisfactorily high viscosity for 1 wt % concentration. They gave good touch after dried. In addition, they dispersed silicone oil better than the composition of Comparative Example 1.

The copolymer of Referential Example 1 having crosslinkage less than that of the present copolymer, and the copolymer of Referential Example 2 having crosslinkage more than that of the present invention both showed lower thickening capability and lower emulsifying capability than those of the present copolymer. The copolymer of Referential Example 3 having the repeating unit (3) less than that of the present copolymer showed stickier touch and lower emulsifying capability. The copolymer of Referential Example 4 having the repeating unit (3) more than that of the present copolymer showed lower thickening capability and lower emulsifying capability than those of the present copolymer. The copolymers of Referential Example 5 and 6 having the repeating unit (1) more or less than that of the present copolymer showed stickier touch and lower emulsifying capability than those of the present copolymer. These copolymers of Referential Examples, however, can be used for cosmetic applications where lower degree of thickening is desired.

Example 10

O/W-Type Cream

| Component | wt % |
|---|---|
| 1. Crosslinked dimethylpolysiloxane (*1) | 10.0 |
| 2. Isotridecyl isononanate | 5.0 |
| 3. Decamethylcyclopolysiloxane | 25.0 |
| 4. Polyether-comodified silicone (*2) | 0.5 |
| 5. Dipropylene glycol | 6.0 |
| 6. Glycerin | 5.0 |
| 7. 2% aqueous solution of methyl cellulose (*3) | 5.0 |
| 8. Polyacrylamide emulsifier (*4) | 2.0 |
| 9. Antiseptic agent | q.s. |
| 10. Perfume | q.s. |
| 11. Neutralized dispersion of Example 1 | 41.5 |

(*1) KSG-15, ex Shin-Etsu Chemical Co. Ltd.
(*2) KF-6011, ex Shin-Etsu Chemical Co. Ltd.
(*3) Metholose SM-4000, ex Shin-Etsu Chemical Co. Ltd.
(*4) Sepigel 305, ex Sepic, Inc.

Method of Preparation

A: Components 5 to 11 were mixed.

B: Components 1 to 4 were mixed, and added to the mixture prepared in A and emulsified.

The cream obtained spread smoothly and gave moisturized and refreshing feel to the skin without stickiness or greasiness.

Example 11

O/W-Type Cream

| Component | wt % |
|---|---|
| 1. Crosslinked dimethylpolysiloxane (*1) | 10.0 |
| 2. Crosslinked dimethylpolysiloxane (*2) | 20.0 |
| 3. Isotridecyl isononanate | 7.5 |
| 4. Decamethylcyclopolysiloxane | 7.0 |
| 5. Polyglycerin-modified branched silicone (*3) | 0.5 |
| 6. Polyglycerin-modified branched silicone (*4) | 0.5 |
| 7. Dipropylene glycol | 6.0 |
| 8. Glycerin | 5.0 |
| 9. Antiseptic agent | q.s. |
| 10. Perfume | q.s. |
| 11. Neutralized dispersion of Example 2(diluted to 3 wt %, as solid, with ion-exchanged water) | 43.5 |

(*1) KSG-15, ex Shin-Etsu Chemical Co. Ltd.
(*2) KSG-16, ex Shin-Etsu Chemical Co. Ltd.
(*3) KF-6100, ex Shin-Etsu Chemical Co. Ltd.
(*4) KF-6104, ex Shin-Etsu Chemical Co. Ltd.

Method of Preparation

A: Components 5 to 11 were mixed.

B: Components 1 to 4 were mixed and added to the mixture prepared in A and emulsified.

The cream obtained had fine texture and spread smoothly. It gave moisturized and refreshing feel to the skin without stickiness or greasiness.

Example 12

O/W-Type Cream

| Component | wt % |
|---|---|
| 1. Crosslinked alkyl-modified dimethylpolysiloxane (*1) | 7.0 |
| 2. Crosslinked dimethylpolysiloxane (*2) | 10.0 |
| 3. Decamethylcyclopentasiloxane | 15.0 |
| 4. Dimethylpolysiloxane(6 mm$^2$/sec (25° C.)) | 10.0 |
| 5. Polyether-modified silicone (*3) | 1.0 |
| 6. Propylene glycol | 3.0 |
| 7. Xanthan gum (2% aqueous solution) | 8.0 |
| 8. Antiseptic agent | q.s. |
| 9. Perfume | q.s. |
| 10. Neutralized dispersion of Example 3 (diluted to 3 wt %, as solid, with ion-exchanged water) | 46.0 |

(*1) KSG-43, ex Shin-Etsu Chemical Co. Ltd.
(*2) KSG-16, ex Shin-Etsu Chemical Co. Ltd.
(*3) KF-6011, ex Shin-Etsu Chemical Co. Ltd.

Method of Preparation

A: Components 1 to 4 were mixed.

B: Components 5 to 10 were mixed.

C: The mixture prepared in A was added to the mixture prepared in B and emulsified.

The cream obtained had fine texture and spread smoothly. It gave moisturized and refreshing feel to the skin without stickiness or greasiness.

Example 13

Hair Cream

| Component | wt % |
|---|---|
| 1. Dimethylpolysiloxane(6 mm$^2$/sec (25° C.)) | 5.0 |
| 2. Mixture of 10 wt % decamethylcyclopentasiloxane and 90 wt % silicone gum having 20,000,000 mm$^2$/s | 10.0 |
| 3. Stearyltrimethylammonium chloride | 1.5 |
| 4. Glycerin | 3.0 |
| 5. Propylene glycol | 5.0 |
| 6. Hydroxyethyl cellulose | 0.2 |
| 7. Antiseptic agent | q.s. |
| 8. Perfume | q.s. |
| 9. Neutralized dispersion of Example 4(diluted to 10 wt %, as solid, with ion-exchanged water) | 75.3 |

Method of Preparation

A: Components 1 and 2 were mixed.

B: Components 3 to 7 and 9 were mixed.

C: The mixture prepared in B was added to the mixture prepared in A and emulsified. After cooling the emulsion obtained, component 8 was added.

The hair cream thus obtained spread smoothly when applied to the hair and gave the hair softness, smoothness, moisturized feel and gloss.

Example 14

O/W-Type UV-Cut Cream

| Component | wt % |
|---|---|
| 1. Crosslinkedorganopolysiloxane (*1) | 5.0 |
| 2. Cetyl isooctanoate | 5.0 |
| 3. Octyl methoxy cinnamate | 2.0 |
| 4. Dispersion of Titanium oxide/ decamethylcyclopentasiloxane (*2) | 15.0 |
| 5. Polyether-modified silicone (*3) | 1.0 |
| 6. Polyether-modified silicone (*4) | 1.0 |
| 7. Mixture of amide acryla (*5) | 2.0 |
| 8. Propylene glycol | 5.0 |
| 9. 2% aqueous solution of methyl cellulose (*6) | 1.0 |
| 10. Antiseptic agent | q.s. |
| 11. Perfume | q.s. |
| 12. Neutralized dispersion of Example 5 | 63.0 |

(*1) KSG-15, ex Shin-Etsu Chemical Co. Ltd.
(*2) SPD-T5, ex Shin-Etsu Chemical Co. Ltd.
(*3) KF-6013, ex Shin-Etsu Chemical Co. Ltd.
(*4) KF-6011, ex Shin-Etsu Chemical Co. Ltd.
(*5) Sepigel 305, ex Sepic, Inc.
(*6) Metholose SM-4000, ex Shin-Etsu Chemical Co. Ltd.

Method of Preparation

A: Components 5 to 9, 10 and 12 were mixed.

B: Components 1 to 3 were mixed while heating. The mixture obtained was added to the mixture prepared in A and emulsified.

C: Component 4 was added to the emulsion prepared in B, to which Component 11 was added and homogenized.

The UV cut cream obtained spread smoothly and gave transparent finish without stickiness or greasiness.

Example 15

W/O-Type Milky Lotion

| Component | wt % |
|---|---|
| 1. Crosslinked polyether-modified silicone (*1) | 5.0 |
| 2. Crosslinked dimethylpolysiloxane (*2) | 5.0 |
| 3. Polyether-modified silicone (*3) | 1.0 |
| 4. Dimethylpolysiloxane (6 mm²/sec(25° C.)) | 8.0 |
| 5. Decamethylcyclopentasiloxane | 13.0 |
| 6. Glyceryl trioctanoate | 5.0 |
| 7. 1,3-butylene glycol | 6.0 |
| 8. Antiseptic agent | q.s. |
| 9. Perfume | q.s. |
| 10. Neutralized dispersion of Example 1 | 57.0 |

(*1) KSG-210, ex Shin-Etsu Chemical Co. Ltd.
(*2) KSG-15, ex Shin-Etsu Chemical Co. Ltd.
(*3) KF-6017, ex Shin-Etsu Chemical Co. Ltd.

Method of Preparation
A: Components 1 to 6 were mixed.
B: Components 8 to 10 were mixed and added to the mixture prepared in A and emulsified.
The milky lotion thus obtained was not sticky and spread smoothly. It showed good affinity to the skin and was comfortable to use.

Example 16

Antiperspirant (Roll-On) Composition

| Component | wt % |
|---|---|
| 1. Polyether-modified silicone (*1) | 0.5 |
| 2. Hydroxy-aluminum chloride | 3.0 |
| 3. Talc | 5.0 |
| 4. Ethyl alcohol | 15.0 |
| 5. Hydroxyethyl cellulose | 2.0 |
| 6. Neutralized dispersion of Example 2 (diluted to 2 wt %, as solid, with ion-exchanged water) | 74.5 |

(*1) KF-6011, ex Shin-Etsu Chemical Co. Ltd.

Method of Preparation
A: Components 1 to 6 were mixed.
B: The mixture obtained in A was fed in a roll-on container.
The antiperspirant thus obtained gave no stickiness when applied to the skin. The applied antiperspirant gave light and smooth touch after air-dried.

Example 17

Shampoo

| Component | wt % |
|---|---|
| 1. 30% aqueous solution of polyoxyethylene (EO: 3) sodium lauryl sulfate | 30.0 |
| 2. Lauryl sulfate diethanolamide | 4.0 |
| 3. Propylene glycol | 2.0 |
| 4. Antiseptic agent, colorant, perfume | q.s. |
| 5. Neutralized dispersion of Example 2 | 64.0 |

Method of Preparation

Component 1-5 were mixed with a mixer.

The shampoo thus obtained gave no stickiness when applied to the hair and smooth touch.

As shown above, the present composition is an excellent thickener and/or an emulsifier for cosmetics comprising oils, particularly silicone oils.

The invention claimed is:

1. An aqueous composition used for cosmetics, characterized in that the composition comprises 0.5 to 50 wt %, based on weight of the composition, of a copolymer having main chains comprising the repeating units represented by the following formula (1), the repeating units represented by the following formula (2), and the repeating units represented by the following formula (3), said main chains being crosslinked by a crosslinking agent,

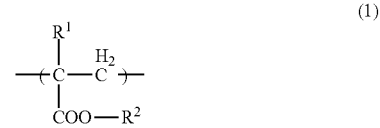

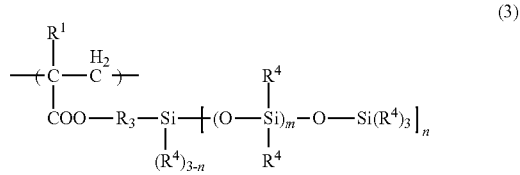

wherein $R^1$ is a hydrogen atom or a hydrocarbon group having 1 to 3 carbon atoms, $R^2$ is a hydrocarbon group having 1 to 24 carbon atoms, $R^3$ is a divalent hydrocarbon group having 1 to 4 carbon atoms, $R^4$ is an aliphatic hydrocarbon group having 1 to 6 carbon atoms or a phenyl group, X is a hydrogen atom, an alkaline metal ion, ammonium ion, or an organic ammonium ion, m of formula (3) is an integer of 10 to 500, and n is an integer of from 1 to 3 wherein the copolymer comprises 25 to 75 wt % of the repeating units represented by the above formula (1), 20 to 60 wt % of the repeating units represented by the above formula (2), 2 to 35 wt % of the repeating units represented by the above formula (3), and 0.05 to 4 wt % of the crosslinking agent, based on weight of the copolymer, and wherein the crosslinking agent is at least one selected from the group consisting of tris(2-(meth)acryloyloxyethyl) isocyanurate, trimethylolpropane tri(meth)acrylate, polyoxyalkylene di(meth)acrylate represented by the following formula (4), and polyorganosiloxane represented by the following formula (5)

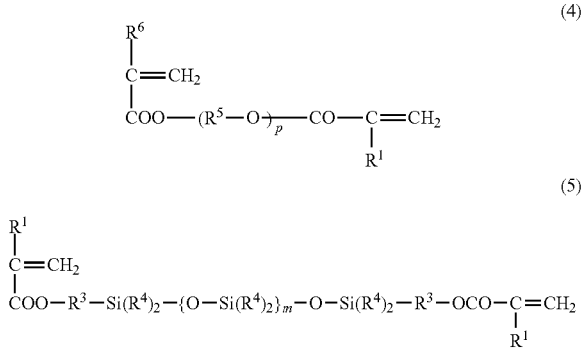

wherein $R^1$, $R^3$, and $R^4$ are as defined above, m of formula (5) is 0 to 500, $R^5$ is a divalent hydrocarbon group having 1 to 4 carbon atoms, $R^6$ is a hydrogen atom or a methyl group, and p is an integer of 1 to 50.

2. The composition according to claim 1, wherein the aqueous composition comprises 10 to 50 wt %, based on weight of the composition, of the copolymer.

3. The composition according to claim 1, wherein $R^1$ is a methyl group, $R^2$ is a methyl or an ethyl group, $R^3$ is a propylene group, and $R^4$ is a methyl group.

4. The composition according to claim 1, wherein n is 1, and m ranges from 10 to 250 on average, in the formula (3).

5. The composition according to claim 1, wherein X is a sodium ion in the formula (2).

6. A cosmetic, characterized in that the cosmetic comprises the composition according to claim 1 in an amount of from 0.1 to 10.0 wt %, as solid, based on total weight of the cosmetic.

7. The cosmetic according to claim 6, wherein the cosmetic further comprises (E) an unctuous agent selected from the group consisting of silicone oils, hydrocarbon oils, ester oils, and glyceride oils.

8. The cosmetic according to claim 6, wherein the cosmetic further comprises (I) a surfactant.

9. The cosmetic according to claim 8, wherein the surfactant (I) is selected from the group consisting of a polyoxyalkylene-modified linear or branched organopolysiloxane, a polyglycerin-modified linear or branched organopolysiloxane, a polyoxyalkylene-alkyl-comodified organopolysiloxane and a polyglycerin-alkyl-comodified organopolysiloxane.

10. The cosmetic according to claim 6, wherein the cosmetic further comprises (K) a composition consisting of a crosslinked organopolysiloxane having a polyether moiety and/or a polyglycerin moiety, and a liquid oil.

11. The cosmetic according to claim 10, wherein the crosslinked organopolysiloxane having a polyether and/or a polyglycerin moiety is the one prepared from a methylhydrogenpolysiloxane grafted with polyoxyethylene chains and/or the one prepared from a methylhydrogenpolysiloxane grafted with polyglycerin chains.

12. The cosmetic according to claim 6, wherein the cosmetic further comprises (L) a silicone resin selected from the group consisting of silicone network compounds containing $SiO_2$ units and/or $RSiO_{1.5}$ units, wherein R is an alkyl group, and linear acryl/silicone graft- or block-copolymer.

13. The cosmetic according to claim 6, wherein the cosmetic is an O/W of cream, foundation, shampoo or rinse.

14. The cosmetic according to claim 6, wherein the cosmetic is in the form of oil-in-water emulsion.

* * * * *